US012064121B2

(12) United States Patent
Baril et al.

(10) Patent No.: US 12,064,121 B2
(45) Date of Patent: Aug. 20, 2024

(54) SURGICAL CLIP PACKS COUPLEABLE TO SURGICAL ACCESS DEVICES

(71) Applicant: Covidien LP, Mansfield, MA (US)

(72) Inventors: Jacob C. Baril, Norwalk, CT (US); Garrett P. Ebersole, Hamden, CT (US); Saumya Banerjee, Hamden, CT (US); Justin J. Thomas, New Haven, CT (US); Roy J. Pilletere, Middletown, CT (US); Matthew A. Dinino, Newington, CT (US); Nicolette L. Roy, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 175 days.

(21) Appl. No.: 17/522,072

(22) Filed: Nov. 9, 2021

(65) Prior Publication Data

US 2022/0160364 A1 May 26, 2022

Related U.S. Application Data

(60) Provisional application No. 63/116,362, filed on Nov. 20, 2020.

(51) Int. Cl.
*A61B 17/122* (2006.01)
*A61B 17/00* (2006.01)
*A61B 17/34* (2006.01)

(52) U.S. Cl.
CPC ........ *A61B 17/122* (2013.01); *A61B 17/1222* (2013.01); *A61B 17/3423* (2013.01); *A61B 2017/00477* (2013.01)

(58) Field of Classification Search
CPC .............. A61B 17/122; A61B 17/1222; A61B 17/3423; A61B 2017/00477; A61B 17/1285; A61B 17/34; A61B 17/115; A61B 17/128; A61B 17/1152; A61B 17/1155; A61B 17/1157; A61B 1/00131
See application file for complete search history.

(56) References Cited

U.S. PATENT DOCUMENTS 4,361,229 A * 11/1982 Mericle ................ A61B 17/122
606/143
5,843,001 A * 12/1998 Goldenberg ......... A61B 10/025
604/533

(Continued)

FOREIGN PATENT DOCUMENTS

WO 2019089300 A2 5/2019
WO 2019173488 A1 9/2019

OTHER PUBLICATIONS

Uwe Delpy et al., "Schnappverbindungen aus Kunststoff In: Schnappverbindungen aus Kunststoff", Verlag, Ehningen bei Boblingen, XP055428286, pp. 1, 2, 9, and 36.

(Continued)

*Primary Examiner* — Shaun L David
*Assistant Examiner* — Rachael L Geiger
(74) *Attorney, Agent, or Firm* — Draft Masters PLLC

(57) ABSTRACT

A surgical clip pack includes a frame configured to engage a portion of a surgical access device. The frame includes a storage compartment and an annulus defining a lumen that has a diameter at least as large as a diameter of an opening of the surgical access device. A receptacle is disposed within the storage compartment and is configured to house a surgical fastener.

22 Claims, 7 Drawing Sheets

(56) References Cited

U.S. PATENT DOCUMENTS

| | | |
|---|---|---|
| 6,419,682 B1 | 7/2002 | Appleby et al. |
| 9,572,568 B2 | 2/2017 | Gorek et al. |
| 2006/0249410 A1* | 11/2006 | Vandenbroek ....... A61B 17/105 |
| | | 206/340 |
| 2021/0298758 A1* | 9/2021 | Thomas ............. A61B 17/1222 |

OTHER PUBLICATIONS

The International Search Report and Written Opinion dated Feb. 18, 2022 issued in corresponding PCT Appln. No. PCT/US2021/058892.

* cited by examiner

SURGICAL CLIP PACKS COUPLEABLE TO SURGICAL ACCESS DEVICES

CROSS-REFERENCE TO RELATED APPLICATION

The present application claims the benefit of and priority to U.S. Provisional Application No. 63/116,362, filed on Nov. 20, 2020. The entire disclosure of the foregoing application is incorporated by reference herein.

FIELD

The present disclosure is generally related to surgical devices. More particularly, this disclosure relates to a surgical clip pack configured to couple to a surgical access device.

BACKGROUND

Many surgical procedures require vessels, veins, or other tissues of the body to be tied, or ligated, during the procedure. Specialized, non-absorbable ligation clips, typically made of a polymer, have been developed for this purpose. The clips are often applied using a single-fire clip applier that applies a clip over vessels laparoscopically. A surgeon needs to remove the single fire clip applier from the surgical working space via a surgical access device, such as a cannula, in order to reload the clip applier with a new ligation clip.

The clips are generally packaged together in small "refill" packs with a couple of clips disposed of therein. The refill packs and the clips may be easily dropped outside the sterile field or may otherwise be lost or misplaced due to their small size and requiring the clinician to obtain a new refill pack. Each dropped or lost clip or refill pack adds to the overall cost of the surgery as each one needs to be replaced. Furthermore, surgeons or medical staff may spend extra time looking for the dropped or misplaced refill packs or clips, unnecessarily extending a surgery. If the surgeon is unfamiliar with the setup in the room, they may not always remember or know where the refill pack is kept causing a small delay looking for the refill pack of clips. Accordingly, a device that keeps the refill packs and therefore the clips within the surgical sterile field that is easily accessible to the surgeon or medical staff in a similar location for any procedure regardless of the surgery or room setup is desirable.

SUMMARY

This disclosure generally relates to a surgical clip pack. The surgical clip pack includes a frame configured to engage a portion of a surgical access device. The frame includes a storage compartment and an annulus defining a lumen that has a diameter at least as large as a diameter of an opening of the surgical access device. A receptacle is disposed within the storage compartment and is configured to house a surgical fastener.

In aspects, the frame may include at least one tab configured to engage a slot disposed on a proximal portion of the surgical access device.

In other aspects, a storage region may be disposed circumferentially about the frame. Each receptacle may be configured to house at least one surgical fastener.

In yet another aspect, the surgical fastener may be a surgical clip.

In another aspect, at least one receptacle of the storage region may be configured to house a surgical fastener of a different size than another surgical fastener housed by at least one other receptacle.

In aspects, the storage compartment may surround about a third of the annulus.

In additional aspects, at least five receptacles may be disposed within the storage compartment.

In disclosed aspects, the receptacle may include a pin disposed within a proximal portion thereof. The pin may be configured to fit within an elbow of a surgical fastener.

In further aspects, the frame may include two tabs. The tabs may include a shelf at distal portions thereof. The shelf may be configured to cause the tabs to flex radially inwards when inserted into a slot of the surgical access device until the shelf exits the slot. The shelf may extend over an edge of the slot thereby securing the surgical clip pack to the surgical access device.

In accordance with another aspect of this disclosure, a surgical clip pack includes a ring configured to couple to a surgical access device. The surgical clip pack also includes an arm coupled to a side of the ring. The arm includes a plurality of receptacles. Each receptacle is configured to house at least one surgical fastener.

In a further aspect, the ring may include tabs configured to engage a slot disposed proximally on the surgical access device.

In further aspects, the ring may include two tabs. The tabs may include a shelf at distal portions thereof. The shelf may be configured to cause the tabs to flex radially inwards when inserted into a slot of the surgical access device until the shelf exits the slot. The shelf may extend over an edge of the slot thereby securing the surgical clip pack to the surgical access device.

In another aspect, the ring may define an aperture that has a diameter that is at least as large as a diameter of a proximal opening of the surgical access device.

In disclosed aspects, the arm may extend circumferentially about at least a portion of the ring.

In additional aspects, the surgical fastener may include bars at distal ends of the arms of the surgical fasteners. The bars may be configured to press against an internal wall of the receptacle to hold the surgical fastener in the receptacle.

In aspects, the surgical fastener may be a surgical clip.

In another aspect, at least one receptacle of the storage region may be configured to house a surgical fastener of a different size than another surgical fastener housed by at least one other receptacle.

In an aspect, each receptacle of the plurality of receptacles may include a pin configured to stabilize the surgical fastener therein.

In yet further aspects, the pin may be configured to fit into an elbow of the surgical fastener such that the pin holds the surgical fastener in the receptacle.

The details of one or more aspects of the disclosure are set forth in the accompanying drawings and the description below. Other features, objects, and advantages of the techniques described in this disclosure will be apparent from the description and drawings, and from the claims.

DESCRIPTION OF DRAWINGS

The accompanying drawings, which are incorporated in and constitute a part of this specification, illustrate aspects and features of the disclosure and, together with the detailed description below, serve to further explain the disclosure, in which.

Figure 1:
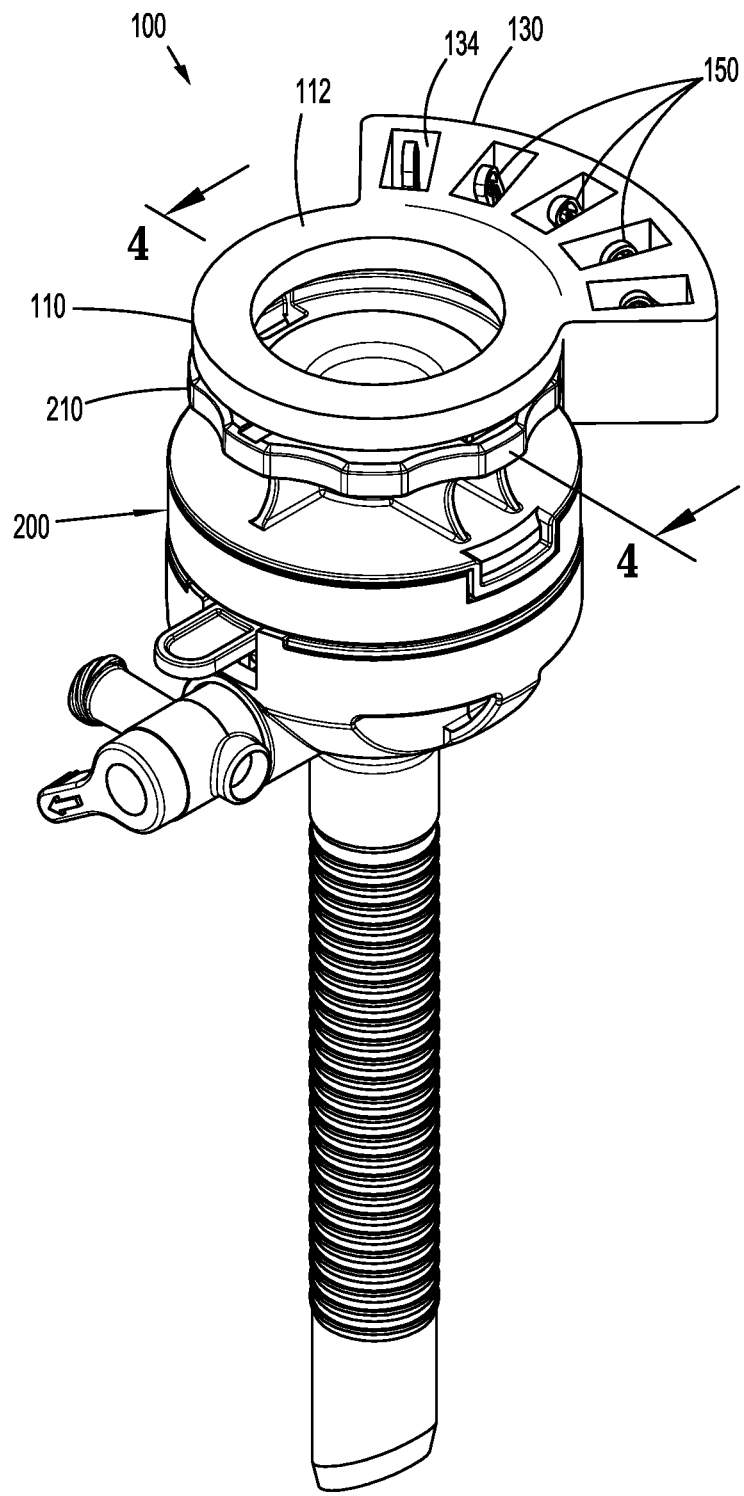
FIG. 1 is a perspective view of a surgical clip pack coupled to a surgical access device.

Further details and various aspects of this disclosure are described in more detail below with reference to the appended figures.

DETAILED DESCRIPTION

Aspects of the presently disclosed surgical clip pack are described in detail with reference to the drawings, in which like reference numerals designate identical or corresponding elements in each of the several views. However, it is to be understood that the disclosed devices are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an illustrative surgical clip pack in accordance with the disclosure should typically be considered as available and applicable to other similar features of another device of the disclosure. Accordingly, technical features described herein in connection with one illustrative surgical clip pack may apply to other devices of the disclosure, and thus duplicative descriptions may be omitted herein.

As used herein the term "distal" refers to that portion of a surgical access device, or component thereof, farther from the user, while the term "proximal" refers to that portion of the surgical access device, or component thereof, closer to the user.

This disclosure relates to a surgical clip pack for storing and providing surgical clips, such as ligation clips. The surgical clip pack is configured to attach to a surgical access device, such as a trocar or cannula such that surgical clips stored in the surgical clip pack are easily accessible. During a surgical procedure, a surgeon can quickly and efficiently reload a single fire surgical clip applier with a new clip from the surgical clip pack. Since the surgical clip pack is coupled to the surgical access device, time is saved that may have otherwise been spent looking for a traditional clip pack having additional surgical clips to reload the surgical clip applier. Further, since the clip pack of this disclosure is coupled to the surgical access device, the opportunity for the additional surgical clips to become contaminated is reduced. While the surgical clip pack is discussed herein with reference to surgical clips, other small devices or instruments used for surgical procedures, such as sutures, needles, or staples may also be stored in and provided by the surgical clip pack.

Figure 2:
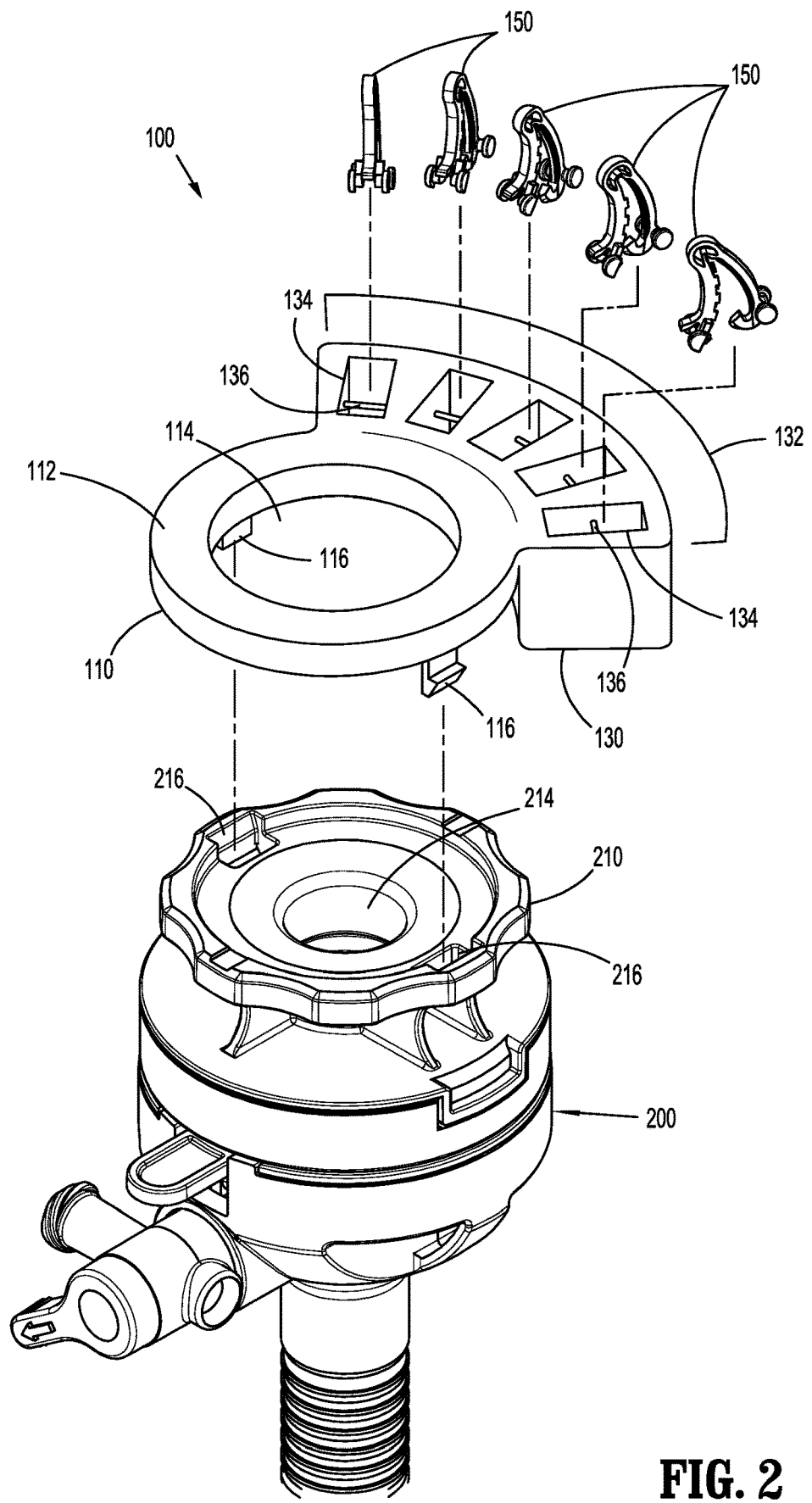
FIG. 2 is an exploded perspective view of the surgical clip pack separated from the surgical access device shown in FIG. 1.

With reference to FIGS. 1 and 2, a surgical clip pack 100 for storing and providing surgical fasteners, such as surgical clips 150, generally includes a frame 110 and a storage compartment 130 extending outwardly from the frame 110. The frame 110 may be an annulus 112 defining a lumen 114. The storage compartment 130 includes a storage region 132 with receptacles 134. In aspects, the storage compartment 130 includes just one receptacle 134. In aspects, storage compartment 130 is an arm extending from the frame 110 and includes at least one receptacle 134. The surgical clip pack 100 provides easy and convenient access to the surgical clips 150 during a surgical procedure.

The surgical clip pack 100 is configured to engage a proximal portion of the surgical access device 200, such as housing 210. The frame 110 includes tabs 116 configured to removably couple to slots 216 of the housing 210. The tabs 116 are configured to snap into the slots 216 such that the surgical clip pack 100 is secured to the surgical access device 200.

The annulus 112 of the frame 110 includes a lumen 114 having a diameter that is at least as large as a diameter of an opening 214 of the housing 210 of the surgical access device 200. The frame 110 is configured such that a surgical instrument may be inserted through the lumen 114 without interference from the surgical clip pack 100.

In aspects, the frame 110 may be "C" shaped and configured to snap onto a tube or cylindrical portion of a surgical access device 200.

Figure 3:
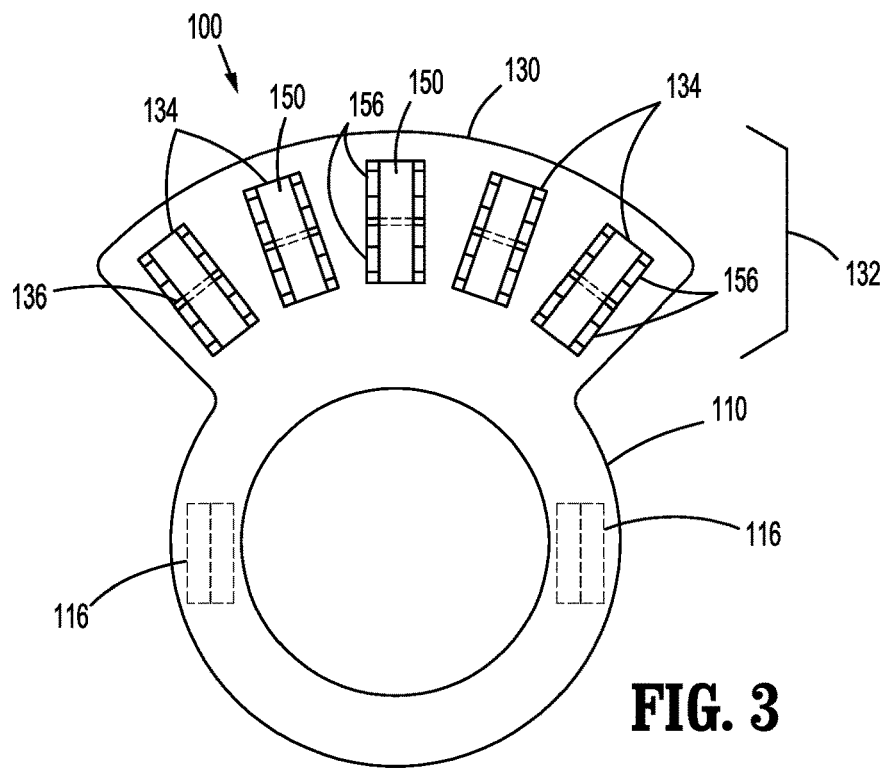
FIG. 3 is a top view of the surgical clip pack of FIGS. 1 and 2.

Referring to FIG. 3, the storage compartment 130 extends from frame 110 and is configured to surround a portion of frame 110. For example, storage compartment 130 surrounds about a third of the frame 110 as illustrated. In aspects, the storage compartment 130 may completely surround the frame 110. The storage region 132 of the storage compartment 130 is arranged about the storage compartment 130 and circumferentially about the frame 110. Each receptacle 134 of the storage region 132 is configured to house a surgical clip 150 (FIG. 2).

In aspects, the storage region 132 includes five receptacles 134 arranged within the storage compartment 130. Each receptacle 134 of the storage region 132 may be configured to house a surgical clip 150 of the same size or surgical clips 150 of varying sizes.

For example, three medium-sized surgical clips 150 may be stored in three separate receptacles 134, one large-sized surgical clip 150 may be stored in another receptacle 134, and a small-sized surgical clip 150 may be stored in a remaining receptacle 134. The number of surgical clips 150 that may be provided by the surgical clip pack 100 may vary depending on the number of receptacles 134 of the storage region 132.

In aspects, sutures, needles, or any other small surgical device may be stored in the storage region 132.

Alternatively, storage compartment 130 may include a single receptacle for housing a traditional packaged clip pack (not shown). For example, a container having clips disposed thereon may be placed into the receptacle 132 of the storage compartment 130 and held in place via a retention mechanism, such as a spring arm.

In yet another aspect, the storage compartment is a cartridge extending from the frame 110 configured to hold surgical fasteners.

Figure 4:
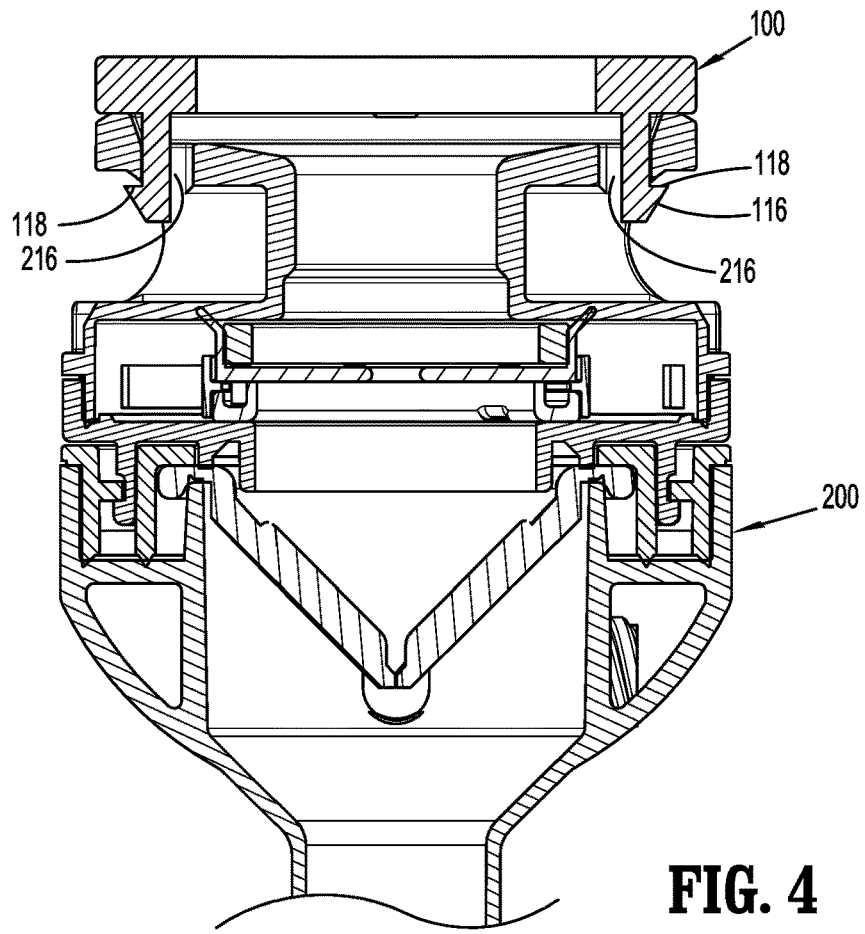
FIG. 4 is a side cross-sectional view of the surgical clip pack coupled to the surgical access device taken along section line 4-4 of FIG. 1.

With reference to FIG. 4, a side cross-sectional view of the surgical clip pack 100 taken along line 4-4 of FIG. 1 is shown. The tabs 116 extending from the frame 110 are configured to couple the surgical clip pack 100 to a housing 210 of the surgical access device 200 via slots 216 of the housing 210. The tabs 116 include a shelf 118, such that, when the tabs 116 are inserted into slot 216, the tabs 116 are flexed radially inwards until the shelf 118 is inserted past an end of slot 216. The tabs 116 then return to an approximately unflexed position, securing the surgical clip pack 100 to the surgical access device 200. To decouple the surgical clip pack 100 from the housing 210 of the surgical access device 200, the tabs 116 are pressed inwards and pushed up such that shelf 118 may pass through slot 216.

In aspects, any tabs or snaps known by those of ordinary skill in the art may be used to couple and secure the surgical clip pack 100 to the surgical access device 200. For example, instead of shelf 118, the tabs 116 may include rounded protrusions at distal ends thereof that snap into rounded cavities of the slots 216 to secure the surgical clip pack 100 to the surgical access device 200 and may be removed with sufficient force pulling on the surgical clip pack 100.

In aspects, the surgical clip pack 100 may include a wrap or seal (not shown) that is removed after coupling the surgical clip pack 100 to the surgical access device 200. In aspects, the wrap or seal covers only a top face of the storage region 132 and receptacles 134. The wrap or seal may be configured to prevent contamination of the surgical clips 150 stored in the surgical clip pack 100. The wrap or seal may be removed in a sterile environment just prior to use.

Figure 5:
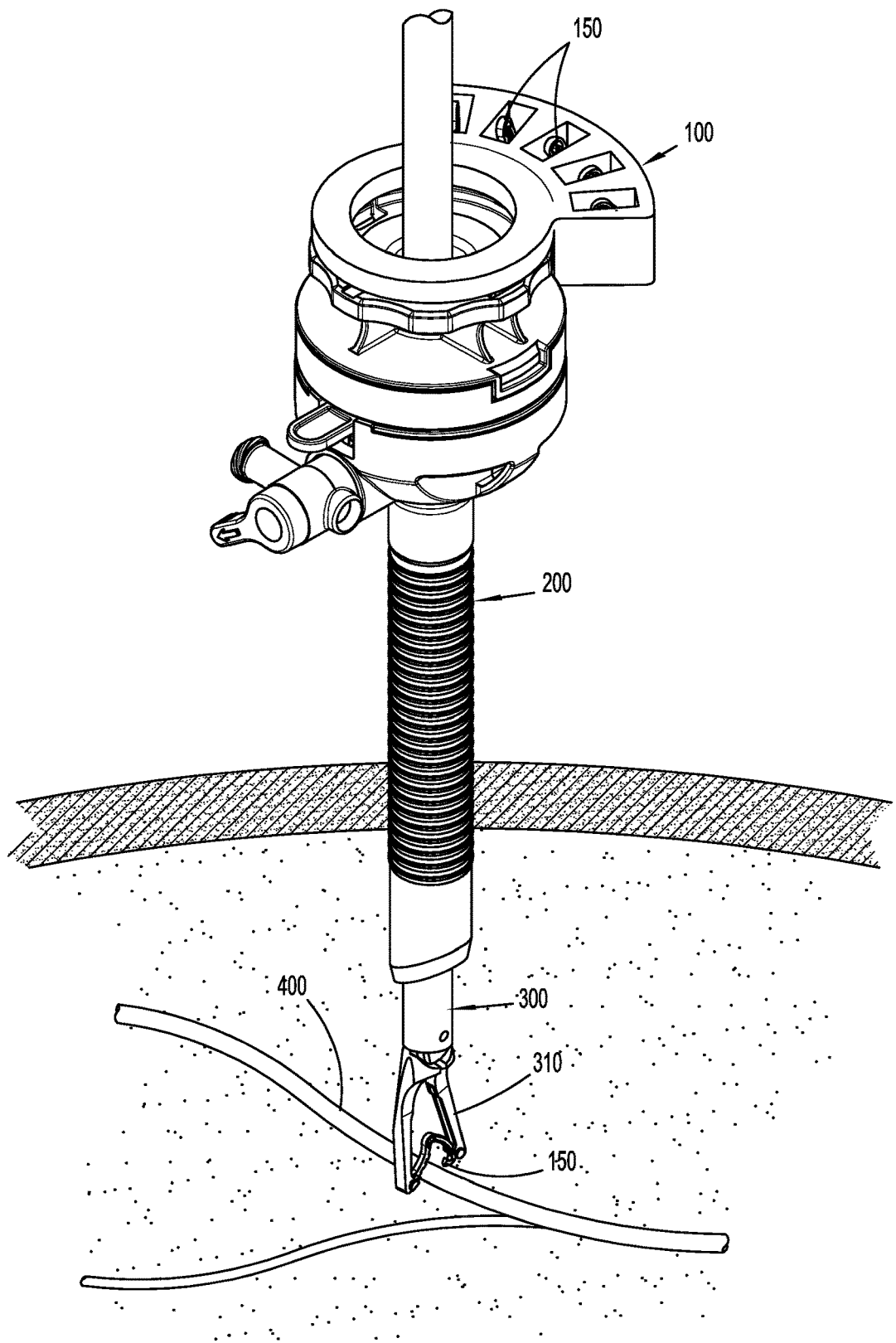
FIG. 5 is a perspective view of a surgical clip applier inserted through the surgical clip pack and surgical access device of FIG. 1.

With reference to FIG. 5, prior to inserting a surgical clip applier 300 into the surgical access device 200, the surgical clip pack 100 is coupled to the surgical access device 200 via the tabs 116 so a surgeon or medical professional has easy access to additional surgical clips 150 or other surgical devices and fasteners. The surgeon may then insert a surgical instrument, such as a surgical clip applier 300, through the lumen 114 of surgical clip pack 100 and through the opening 214 into a lumen of the surgical access device 200. The surgeon or medical professional may clamp or otherwise restrict vessels, veins, arteries, or other tissues using a surgical clip 150 via the surgical clip applier 300. A surgical clip 150 is applied to a vascular structure 400 using the surgical clip applier 300.

Figure 7:
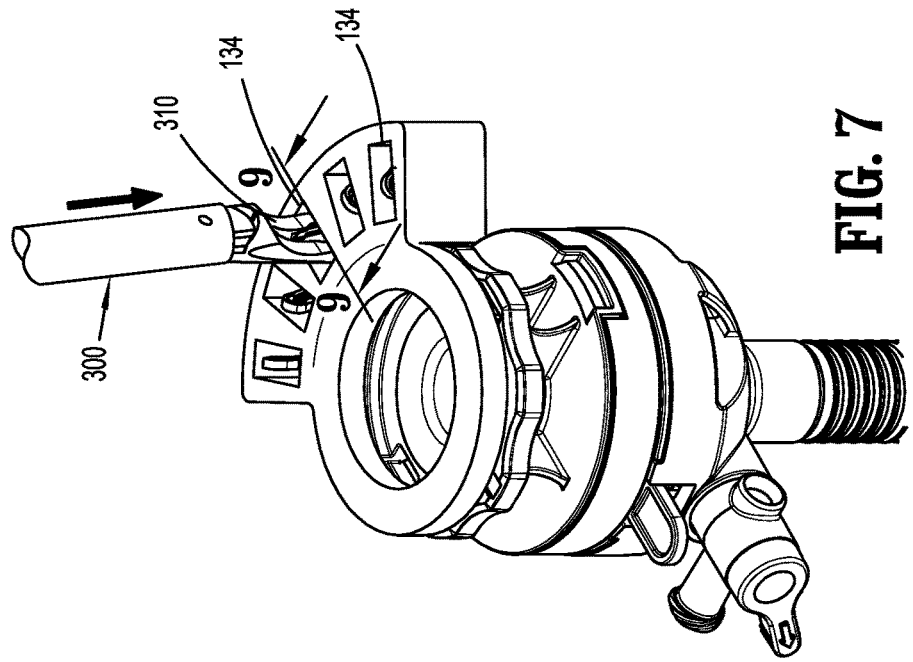
FIG. 7 is a perspective view of a surgical clip applier being reloaded with a clip stored in the surgical clip pack of FIG. 1.
Figure 6:
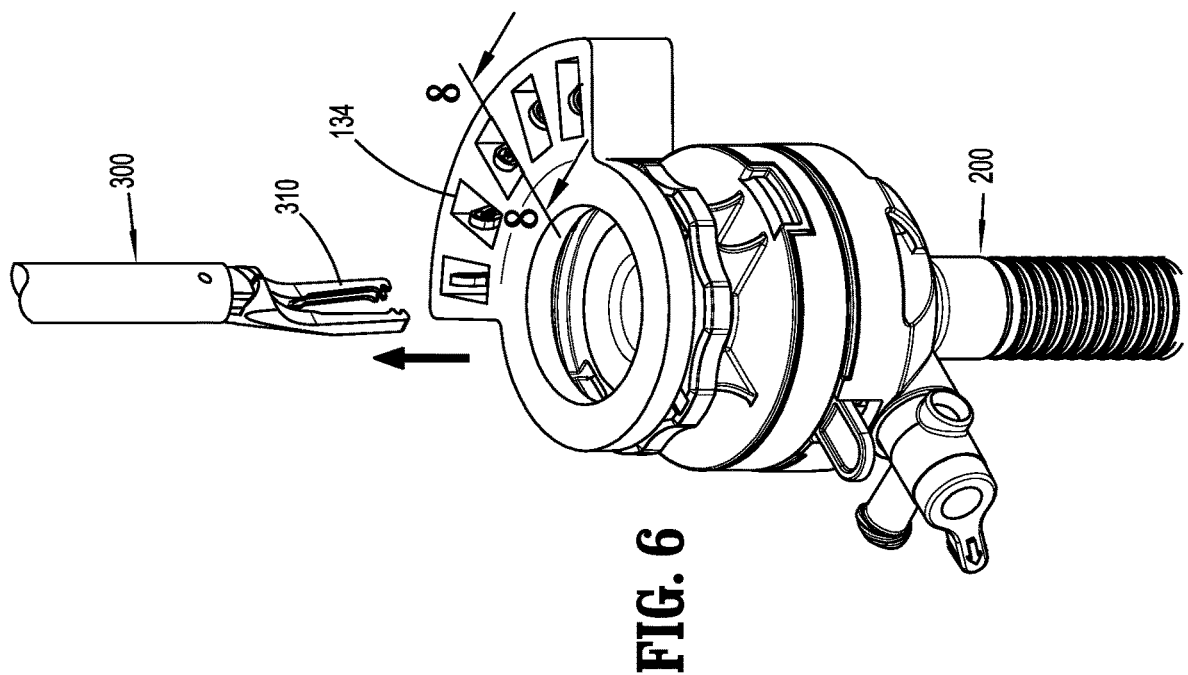
FIG. 6 is a perspective view of the surgical clip applier removed from the surgical clip pack and surgical access device of FIG. 1.

With reference to FIGS. 6 and 7, the surgeon or medical professional then removes the surgical clip applier 300 from the surgical access device 200 and surgical clip pack 100, so that the surgical clip applier 300 may be reloaded with a new surgical clip 150. Since the surgical clip pack 100 is near the operation site, the surgical clip applier 300 is easily reloaded with additional surgical clips 150 while cutting down on time spent looking for additional clips in the operating room. The surgical clip applier 300 is reloaded by inserting the surgical clip applier 300 into a receptacle 134 to grasp a surgical clip 150 stored therein. Since the surgical clip applier 300 may be reloaded by inserting a distal end of the surgical clip applier 300 into a receptacle 134 having a surgical fastener 150 stored therein, the chances a surgical clip 150 is dropped and thereby contaminated is reduced.

Figure 9:
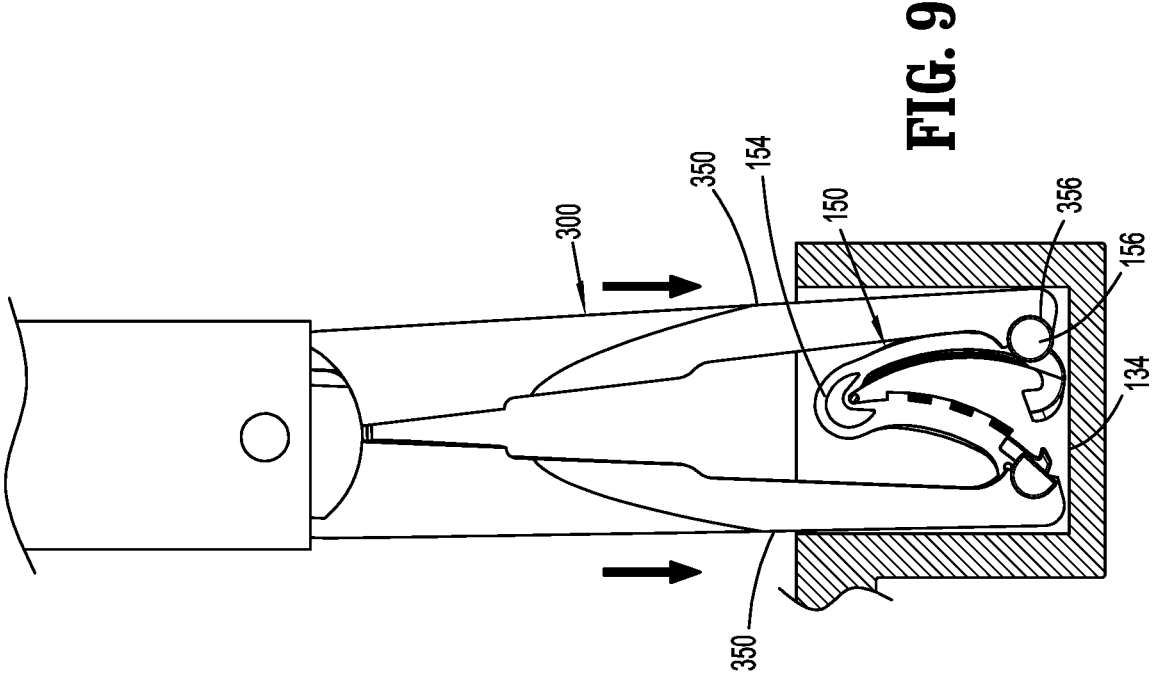
FIG. 9 is a side cross-sectional view taken along section line 9-9 of FIG. 7.
Figure 8:
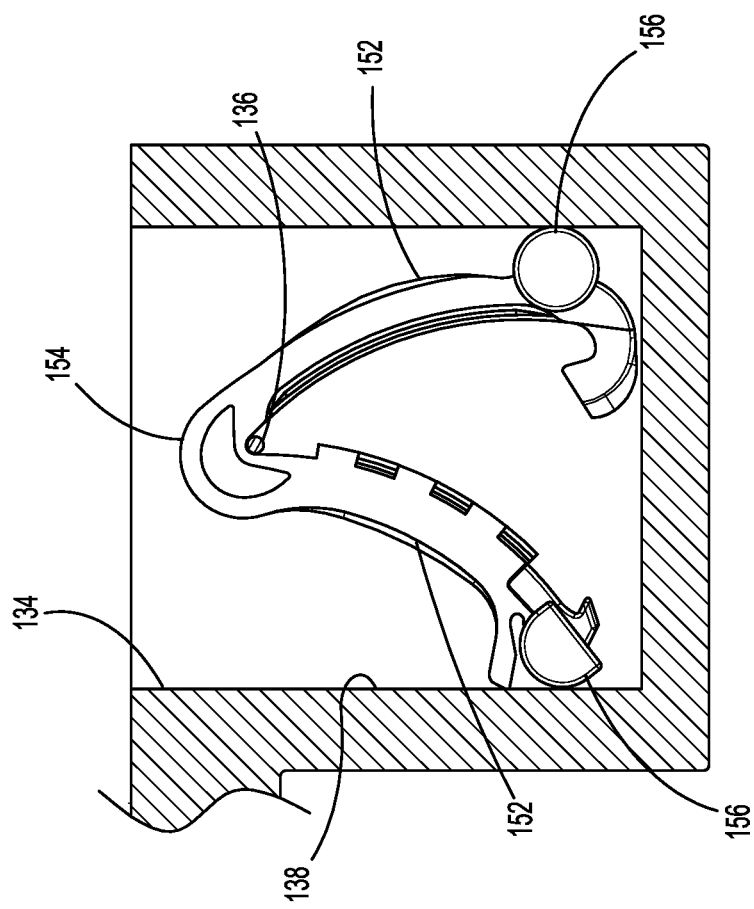
FIG. 8 is a side cross-sectional view taken along section line 8-8 of FIG. 6.

With reference to FIGS. 8 and 9, side views of the receptacles 134 taken along lines 8-8 and 9-9 of FIGS. 6 and 7, respectively, are shown. Each receptacle 134 may include a pin 136 disposed near an upper portion of the receptacle 134 and configured to hold a surgical clip 150. Each arm 152 of a surgical clip 150 would be positioned on either side of the pin 136, and the pin 136 tucked into an elbow 154 of the surgical clip 150. Thus, the pin 136 helps stabilize the surgical clip 150 within the receptacle 134. In aspects, the pin 136 holds the surgical clip 150 within the receptacle 134 via a friction fit with the elbow 154 of the surgical clip.

The arms 152 of the surgical clip 150 are slightly depressed within the receptacle 134. The arms 152 may press outward against the internal walls 138 of the receptacle 134 with sufficient force to hold the surgical clip 150 in the receptacle 134 (i.e., friction fit). The distal ends of the arms 152 may include bars 156 configured to fit with notches 356 of jaws 350 of the surgical clip applier 300. In aspects, the distal ends of the surgical clip 150 or the bars 156, may be pressed against the internal walls 138 of the receptacle 134 with sufficient force to hold the surgical clip 150 in receptacle 134.

As the surgeon or medical professional inserts the clip applier 300 into the receptacle 134 to reload the surgical clip applier 300 with the new surgical clip 150, the jaws 350 of the surgical clip applier 300 further depress the surgical clip arms 152 towards one another. The jaws 350 are then in a partially closed configuration as illustrated. The surgeon continues to insert the surgical clip applier 300 into the receptacle 134 until the notches 356 engage the bars 156, thus securing the surgical clip 150 in the jaws 350.

Figure 10:
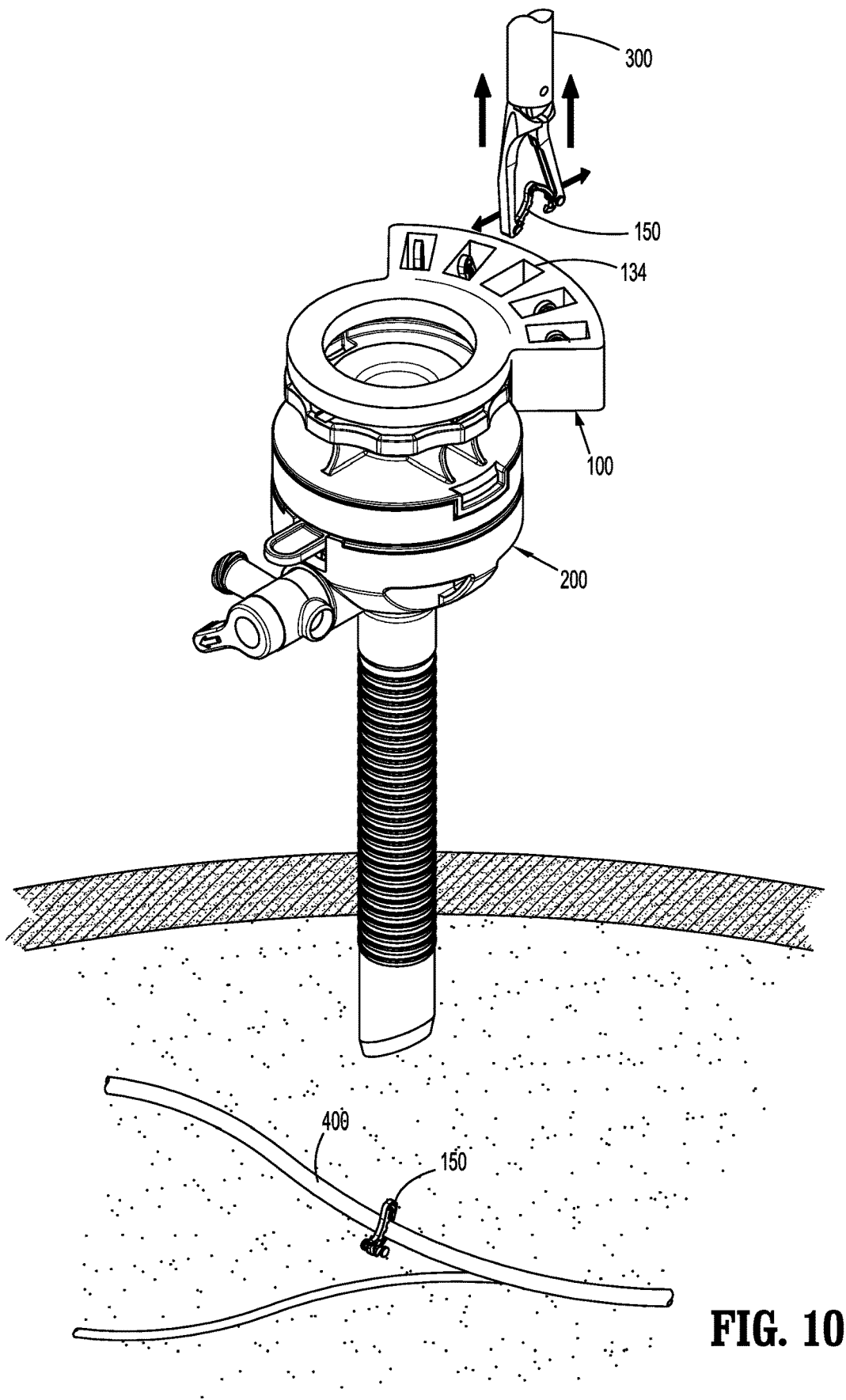
FIG. 10 is a perspective view of the reloaded surgical clip applier removed from a receptacle of the surgical clip pack.

With reference to FIG. 10, after the surgical clip 150 is secured by the jaws 350, the surgeon may remove the surgical clip applier 300. The jaws 350 may be extended into an open position, thus pulling the arms 152 away from each such that they are no longer depressed. The surgeon then repeats the process by inserting the surgical clip applier 300 into the surgical clip pack 100 and surgical access device 200 to apply the surgical clip 150 as needed.

Persons skilled in the art will understand that the devices specifically described herein and illustrated in the accompanying drawings are non-limiting exemplary aspects of the disclosure. It is envisioned that the elements and features illustrated or described in connection with one exemplary aspect may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:
1. A surgical clip pack comprising:
a frame configured to engage a portion of a surgical access device, the frame including:
a storage compartment; and
an annulus having an inner perimeter and an outer perimeter, the inner perimeter defining a lumen, the storage compartment supported on the frame and positioned outwardly of the outer perimeter of the annulus, the storage compartment defining a plurality of receptacles; and a plurality of surgical fasteners, each of the plurality of surgical fasteners received within one of the plurality of receptacles.

2. The surgical clip pack of claim 1, wherein the frame includes at least one tab configured to be releasably received within a slot disposed on a proximal portion of the surgical access device to releasably couple the surgical clip pack to the surgical access device.

3. The surgical clip pack of claim 2, wherein the plurality of receptacles are disposed circumferentially about the frame.

4. The surgical clip pack of claim 3, wherein each of the plurality of surgical fasteners is a surgical clip.

5. The surgical clip pack of claim 1, wherein each of the plurality of surgical fasteners is a surgical clip.

6. The surgical clip pack of claim 3, wherein at least one receptacle of the plurality of receptacles is configured to house a surgical fastener of a different size than another surgical fastener housed by at least one other receptacle of the plurality of receptacles.

7. The surgical clip pack of claim 1, wherein the storage compartment surrounds about a third of the annulus.

8. The surgical clip pack of claim 7, wherein the plurality of receptacles includes at least five receptacles disposed within the storage compartment.

9. The surgical clip pack of claim 1, wherein the receptacle includes a pin disposed within a proximal portion of the receptacle and is configured to fit within an elbow of the surgical fastener.

10. The surgical clip pack of claim 2, further including two tabs, wherein each tab includes a shelf at a distal portion of the tab;

wherein the shelf is configured to cause the tab to flex radially inwards when inserted into the slot of the surgical access device until the shelf exits the slot, the shelf extending over an edge of the slot thereby securing the surgical clip pack to the surgical access device.

11. A surgical clip pack comprising:

a ring having an inner perimeter and an outer perimeter, the inner perimeter defining a lumen, the ring supporting coupling structure configured to releasably couple the ring to a surgical access device;

a compartment coupled to the ring and positioned radially outward of the outer perimeter, the compartment defining a plurality of receptacles; and a plurality of surgical fasteners, one of the plurality of surgical fasteners received within each of the plurality of receptacles.

12. The surgical clip pack of claim 11, wherein the coupling structure of the ring includes tabs configured to be received within a slot disposed proximally on the surgical access device.

13. The surgical clip pack of claim 12, wherein the coupling structure includes two tabs, each of the two tabs including a shelf at a distal portion of the tab and the shelf configured to cause the tab to flex radially inwards when inserted into the slot of the surgical access device until the shelf exits the slot, the shelf extending over an edge of the slot thereby securing the surgical clip pack to the surgical access device.

14. The surgical clip pack of claim 11, wherein the lumen has a diameter that is at least as large as a diameter of a proximal opening of the surgical access device.

15. The surgical clip pack of claim 11, wherein the compartment extends circumferentially about at least a portion of the ring.

16. The surgical clip pack of claim 11, wherein each of the plurality of surgical fasteners includes bars at distal ends of the surgical fastener, the bars configured to press against an internal wall of a respective one of the plurality of receptacles to hold the surgical fastener in the receptacle.

17. The surgical clip pack of claim 11, wherein the surgical fastener is a surgical clip.

18. The surgical clip pack of claim 11, wherein at least one receptacle of the plurality of receptacles is configured to house a surgical fastener of a different size than another surgical fastener housed by at least one other receptacle of the plurality of receptacles.

19. The surgical clip pack of claim 11, wherein each receptacle of the plurality of receptacles includes a pin configured to stabilize the surgical fastener within the receptacle of the plurality of receptacles.

20. The surgical clip pack of claim 19, wherein the pin is configured to fit into an elbow of the surgical fastener such that the pin holds the surgical fastener in the receptacle of the plurality of receptacles.

21. A surgical access device and clip pack assembly comprising:

a surgical access device including a housing, the housing defining an opening and a channel that communicates with the opening; and a surgical clip pack including a ring, a compartment, and a plurality of surgical fasteners, the ring positioned about the opening defined by the housing of the surgical access device and having an inner perimeter and an outer perimeter, the inner perimeter of the ring defining a lumen, the ring supporting coupling structure configured to engage the housing of the surgical access device to releasably couple the ring to the surgical access device, the compartment coupled to the outer perimeter of the ring radially outward of the lumen and defining a plurality of receptacles, each the plurality of surgical fasteners received within one of the plurality of receptacles.

22. The surgical access device of claim 21, wherein the housing of the surgical access device defines slots and the coupling structure of the surgical clip pack includes flexible tabs that are received within the slots to releasably secure the surgical clip pack to the surgical access device.

* * * * *